United States Patent
Petersen et al.

(10) Patent No.: US 6,682,649 B1
(45) Date of Patent: Jan. 27, 2004

(54) SUBSTRATE AND A METHOD FOR DETERMINING AND/OR MONITORING ELECTROPHYSIOLOGICAL PROPERTIES OF ION CHANNELS

(75) Inventors: Jon Wulff Petersen, Lyngby (DK); Pieter Telleman, Lyngby (DK); Ole Hansen, Lyngby (DK); Palle Christophersen, Ballerup (DK); Morten Bech, Ballerup (DK); Soren Peter Olesen, Ballerup (DK); Jorgen Due, Ballerup (DK); Lars Thomsen, Ballerup (DK)

(73) Assignee: Sophion Bioscience A/S, Ballerup (DK)

( * ) Notice: Subject to any disclaimer, the term of this patent is extended or adjusted under 35 U.S.C. 154(b) by 276 days.

(21) Appl. No.: 09/676,814

(22) Filed: Oct. 2, 2000

Related U.S. Application Data
(60) Provisional application No. 60/157,847, filed on Oct. 6, 1999.

(30) Foreign Application Priority Data

Oct. 1, 1999  (DK) ......................................... 1999 01407

(51) Int. Cl.[7] ............................................. G01N 27/327
(52) U.S. Cl. .............................. 205/777.5; 204/403.01; 422/82.01
(58) Field of Search ....................... 204/403.01, 403.13, 204/403.03; 205/777.5, 792; 422/82.01, 82.02

(56) References Cited

U.S. PATENT DOCUMENTS 4,055,799 A * 10/1977 Coster et al. ............... 324/71.1
4,062,750 A    12/1977 Butler (List continued on next page.)

FOREIGN PATENT DOCUMENTS

| DE | 199 36 302 A1 | 2/2001 |
|---|---|---|
| EP | 0299778 A2 | 1/1989 |
| EP | 0299779 A2 | 1/1989 |
| WO | WO 92/21020 | 11/1992 |
| WO | WO 9415701 | 7/1994 |
| WO | WO 9425862 | 11/1994 |
| WO | WO 9746882 | 12/1997 |
| WO | WO 9854294 | 12/1998 |

(List continued on next page.)

OTHER PUBLICATIONS

Kostyuk et al, Nature, vol. 257, 1975, pp. 691–693.*
Neher et al., Pflügers Arch. European Journal of Physiology; vol. 375, pp. 219–228 (1978).

(List continued on next page.)

*Primary Examiner*—Kaj K. Olsen
(74) *Attorney, Agent, or Firm*—Birch, Stewart, Kolasch & Birch, LLP

(57) ABSTRACT

The present invention relates to a substrate and a method for obtaining an electrophysiological measuring configuration in which a cell forms a high resistive seal (giga-seal) around a measuring electrode making it suitable for determining and monitoring a current flow through the cell membrane. The substrate is typically part of an apparatus for studying electrical events in cell membranes, such as an apparatus for carrying out patch clamp techniques utilised to study ion transfer channels in biological membranes. The substrate has a plurality or an array of measuring sites with integrated measuring and reference electrodes formed by wafer processing technology. The electrodes are adapted to conduct a current between them by delivery of ions by one electrode and receipt of ions by the other electrode and are typically silver/silver halide electrodes. This allows for effective and fast measuring of cells in configurations where the there is a direct electrical connection between the measuring electrode and the cell interior, a whole-cell measuring configuration.

28 Claims, 4 Drawing Sheets

U.S. PATENT DOCUMENTS

| | | | |
|---|---|---|---|
| 4,225,410 A | | 9/1980 | Pace |
| 5,164,319 A | | 11/1992 | Hafeman et al. |
| 5,187,096 A | | 2/1993 | Giaever et al. |
| 5,393,401 A | | 2/1995 | Knoll |
| 6,267,872 B1 | * | 7/2001 | Akeson et al. ............... 205/775 |
| 6,315,940 B1 | * | 11/2001 | Nisch et al. ............. 435/287.1 |
| 6,488,829 B1 | * | 12/2002 | Schroeder et al. ...... 204/403.01 |
| 2002/0104757 A1 | * | 8/2002 | Schmidt ..................... 204/418 |
| 2002/0144905 A1 | * | 10/2002 | Schmidt ................ 204/403.01 |
| 2003/0052002 A1 | * | 3/2003 | Vogel et al. ........... 204/403.01 |
| 2003/0098248 A1 | * | 5/2003 | Vogel et al. ............. 205/777.5 |
| 2003/0146091 A1 | * | 8/2003 | Vogel et al. ........... 204/403.01 |

FOREIGN PATENT DOCUMENTS

| | | |
|---|---|---|
| WO | WO 9931503 | 6/1999 |
| WO | WO 9934202 | 7/1999 |
| WO | WO 9966329 | 12/1999 |
| WO | WO 0025121 | 5/2000 |
| WO | WO 01/27614 A1 | 4/2001 |
| WO | WO 01/59447 | 8/2001 |

OTHER PUBLICATIONS

Julie E. M. McGeoch et al., Brain Research; vol. 766, pp. 188–194 (1997).

J. E. M. McGeoch et al., Medical & Biological Engineering & Computing 2000; vol. 38, pp. 113–119 (2000).

O. P. Hamill et al., Pfugers Arch. European Journal of Physiology; vol. 391, pp. 85–100 (1981).

M. Muellenborn et al., The $8^{th}$ International Conference on Solid–State Sensors and Actuators, and Eurosensors IX, Stockholm, Sweden, Jun. 25–29, 1995, pp. 166–169.

James C. Weaver, IEEE Transactions on Plasma Science, vol. 28, No. 1, Feb. 2000, pp. 24–33.

Derwent Abstract for DE 41 15 414 A Nov. 12, 1992.

* cited by examiner

SUBSTRATE AND A METHOD FOR DETERMINING AND/OR MONITORING ELECTROPHYSIOLOGICAL PROPERTIES OF ION CHANNELS

This application claims the benefit of Provisional application No. 60/157,847 filed Oct. 6, 1999

TECHNICAL FIELD

The present invention relates to a substrate and a method for determining and/or monitoring electrophysiological properties of ion channels of ion channel-containing structures, typically lipid membrane-containing structures such as cells, by establishing an electrophysiological measuring configuration in which a cell membrane forms a high resistive seal around a measuring electrode, making it possible to determine and monitor a current flow through the cell membrane. The substrate is typically part of an apparatus for studying electrical events in cell membranes, such as an apparatus for carrying out patch clamp techniques utilised to study ion transfer channels in biological membranes. More particularly, the invention relates to a substrate for such patch clamp apparatus having high through-put and utilising only small amounts of test compounds, only small amounts of liquid carrier, and being capable of carrying out many tests in a short period of time by performing parallel tests on a number of cells simultaneously and independently.

BACKGROUND ART

The general idea of electrically insulating a patch of membrane and studying the ion channels in that patch under voltage-clamp conditions was outlined by Neher, Sakmann, and Steinback in "The Extracellular Patch Clamp, A Method For Resolving Currents Through Individual Open Channels In Biological Membranes", Pflueger Arch. 375; 219–278, 1978. They found that, by pressing a pipette containing acetylcholine (ACh) against the surface of a muscle cell membrane, they could see discrete jumps in electrical current that were attributable to the opening and closing of ACh-activated ion channels. However, they were limited in their work by the fact that the resistance of the seal between the glass of the pipette and the membrane (10–50 M$\Omega$) was very small relative to the resistance of the channel (10 G$\Omega$). The electrical noise resulting from such a seal is inversely related to the resistance and was large enough to obscure the currents flowing through ion channels, the conductance of which are smaller than that of the ACh channel. It also prohibited the clamping of the voltage in the pipette to values different from that of the bath due to the large currents through the seal that would result.

It was then discovered that by fire polishing the glass pipettes and by applying suction to the interior of the pipette a seal of very high resistance (1–100 G$\Omega$) could be obtained with the surface of the cell. This Giga-seal reduced the noise by an order of magnitude to levels at which most channels of biological interest can be studied and greatly extended the voltage range over which these studies could be made. This improved seal has been termed a "giga-seal", and the pipette has been termed a "patch pipette". A more detailed description of the giga-seal may be found in O. P. Hamill, A. Marty, E. Neher, B. Sakmann & F. J. Sigworth: Improved patch-clamp techniques for high resolution current recordings from cells and cell-free membrane patches. Pflügers Arch. 391, 85–100, 1981. For their work in developing the patch clamp technique, Neher and Sakmann were awarded the 1991 Nobel Prize in Physiology and Medicine.

Ion channels are transmembrane proteins which catalyse transport of inorganic ions across cell membranes. The ion channels participate in processes as diverse as gener-ating and timing action potentials, synaptic transmission, secretion of hormones, contraction of muscles, etc. Many drugs exert their specific effects via modulation of ion channels. Examples are antiepileptic compounds like phenytoin and lamotrigine which block voltage-dependent $Na^+$-channels in the brain, antihypertensive drugs like nifedipine and diltiazem which block voltage dependent $Ca^{2+}$-channels in smooth muscle cells, and stimulators of insulin release like glibenclamide and tolbutamide which block an ATP-regulated $K^+$-channel in the pancreas. In addition to chemically induced modulation of ion-channel activity, the patch clamp technique has enabled scientists to perform manipulations with voltage dependent channels. These techniques include adjusting the polarity of the electrode in the patch pipette and altering the saline composition to moderate the free ion levels in the bath solution.

The patch clamp technique represents a major development in biology and medicine, since this technique allows measurement of ion flow through single ion channel proteins, and also allows the study of the single ion channel responses to drugs. Briefly, in standard patch clamp technique, a thin (app. 0.5–2 $\mu$m in diameter) glass pipette is used. The tip of this patch pipette is pressed against the surface of the cell membrane. The pipette tip seals tightly to the cell and isolates a few ion channel proteins in a tiny patch of membrane. The activity of these channels can be measured individually (single channel recording) or, alternatively, the patch can be ruptured allowing measurements of the channel activity of the entire cell membrane (whole cell recording). High-conductance access to the cell interior for performing measurements can be obtained, e.g., by rupturing the membrane by applying subatmospheric pressure in the pipette.

During both single channel recording and whole-cell recording, the activity of individual channel subtypes can be characterised by imposing a "voltage clamp" across the membrane. In the voltage clamp technique the membrane current is recorded at a constant membrane potential. Or—to be more precise—the amplifier supplies exactly the current, which is necessary to keep the membrane potential at a level determined by the experimenter. Hence, currents resulting from opening and closing of ion channels are not allowed to recharge the membrane.

FIG. 1 shows a simplified diagram of the basic operation of a standard prior art voltage clamp amplifier such as the EPC-9 amplifier from HEKA Elektronik. An electrode 6 inside a pipette 4 is connected to the negative terminal of a feedback amplifier, while the clamping voltage (referred to a grounded bath electrode (8)) is connected to a positive terminal (from Stim. In.) and made available at a voltage monitor output. Since the measured pipette voltage and the clamp voltage are supposed to be identical, a correction potential is constantly supplied at the pipette electrode as a current forced through the large feedback resistor. After inversion, the current is made available as an analogue voltage at the Current Monitor output.

The time resolution and voltage control in such experiments are impressive, often in the msec or even $\mu$sec range. However, a major obstacle of the patch clamp technique as a general method in pharmacological screening has been the limited number of compounds that could be tested per day (typically no more than 1 or 2). Also, the very slow rate of solution change that can be accomplished around cells and patches may constitute a major obstacle.

A major limitation determining the throughput of the patch clamp technique is localisation and clamping of cells and pipette, and the nature of the feeding system, which leads the dissolved compound to cells and patches.

In usual patch clamp setups, cells are placed in experimental chambers which are continuously perfused with a physiological salt solution. The establishment of the cell-pipette connection in these chambers is time-consuming and troublesome. Compounds are applied by changing the inlet to a valve connected to a small number of feeding bottles. The required volumes of the supporting liquid and the sample to be tested are high. High throughput systems for performing patch clamp measurements have been proposed, which typically consist of a substrate with a plurality of sites adapted to hold cells in a measuring configuration where the electrical properties of the cell membrane can be determined.

U.S. Pat. No. 5,187,096, Rensselaer, discloses an apparatus for monitoring cell-substrate impedance of cells. Cells are cultured directly on the electrodes which are then covered with a plurality of cells, thus, measurements on individual cells can not be performed.

WO 98/54294, Leland Stanford, discloses a substrate with wells containing electrode arrays. The substrate with wells and electrodes (metal electrodes) is made of silicon using CVD (Chemical Vapor Deposition) and etching techniques and comprises Silicon Nitride "passivation" layers surrounding the electrodes. The cells are cultivated directly on the electrode array. The substrate is adapted to measure electrophysiological properties and discloses a variety of proposed measuring schemes.

WO 99/66329, Cenes, discloses a substrate with perforations arranged in wells and electrodes provided on each side of the substrate. The substrate is made by perforating a silicon substrate with a laser and may be coated with anti-adhesive material on the surface. The substrate is adapted to establish giga seals with cells by positioning the cells on the perforations using suction creating a liquid flow through the perforations, providing the anti-adhesion layer surrounding the perforations, or by guiding the cells electrically. The cells can be permeabilised by EM fields or chemical methods in order to provide a whole-cell measuring configuration. All perforations, and hence all measurable cells, in a well share one working electrode and one reference electrode, see FIG. 1, hence measurements on individual cells can not be performed.

WO 99/31503, Vogel et al., discloses a measuring device with an aperture arranged in a well on a substrate (carrier) and separating two compartments. The measuring device comprises two electrodes positioned on either side of the aperture and adapted to position a cell at the aperture opening. The substrate may have hydrophobic and hydrophilic regions in order to guide the positioning of the cells at the aperture opening.

SUMMARY OF THE INVENTION

The present invention provides a substrate and a method optimised for determining or monitoring current flow through ion channel-containing structures such as cell membranes, with a high throughput and reliability and under conditions that are realistic with respect to the influences to which the cells or cell membranes are subjected. Thus, the results determined using the substrate and the method of the invention, e.g., variations in ion channel activity as a result of influencing the cell membrane with, e.g., various test compounds, can be relied upon as true manifestations of the influences proper and not of artefacts introduced by the measuring system, and can be used as a valid basis for studying electrophysiological phenomena related to the conductivity or capacitance of cell membranes under given conditions.

This is because the current through one or more ion channels is directly measured using reversible electrodes as characterized below, typically silver/silver halide electrodes such as silver chloride electrodes, as both measuring electrodes and reference electrodes.

The substrate and method of the invention may be used not only for measurements on cell membranes, but also on other ion channel-containing structures, such as artificial membranes. The invention permits performing several tests, such as electrophysilogical measurements on ion transfer channels and membranes, simultaneously and independently. The substrate of the invention constitutes a complete and easily handled microsystem which uses only small amounts of supporting liquid (a physiological salt solution, isotonic with the cells, that is, normally having an osmolarity of 150 millimolar NaCl or another suitable salt) and small amounts of test samples.

In one aspect, the invention relates to a plane substrate having an first surface part and an opposite second surface part, the first surface part having a plurality of sites each of which is adapted to hold an ion channel-containing structure, each site having a measuring electrode associated therewith, the substrate carrying one or more reference electrodes, the measuring electrodes and the respective reference electrode or reference electrodes being electrodes capable of generating, when in electrolytic contact with each other and when a potential difference is applied between them, a current between them by delivery of ions by one electrode and receipt of ions by the other electrode, each of the sites being adapted to provide a high electrical resistance seal between an ion channel-containing structure held at the site and a surface part of the site, the seal, when provided, separating a domain defined on one side of the ion channel-containing structure and in electrolytic contact with the measuring electrode from a domain defined on the other side of the ion channel-containing structure and in electrolytic contact with the respective reference electrode so that a current flowing through ion channels of the ion channel-containing structure between the electrodes can be determined and/or monitored, the electrodes being integrated with the substrate and having been formed by a wafer processing technology.

In another aspect, the invention relates to a method method of establishing a whole cell measuring configuration for determining and/or monitoring an electrophysiological property of one or more ion channels of one or more ion channel-containing structures, said method comprising the steps of providing a substrate as defined above, supplying a carrier liquid at one or more sites, said carrier liquid containing one or more ion channel-containing structures, positioning at least one of the ion channel-containing structures at a corresponding number of sites, checking for a high electrical resistance seal between an ion channel-containing structure held at a site and the surface part of the site with which the high electrical resistance seal is to be provided by successively applying a first electric potential difference between the measuring electrode associated with the site and a reference electrode, monitoring a first current flowing between said measuring electrode and said reference electrode, and comparing said first current to a predetermined threshold current and, if the first current is at most the predetermined threshold current, then approving the site as having an acceptable seal between the ion cannel-containing structure and the surface part of the site, and establishing a whole-cell configuration at approved sites, whereby a third current flowing through ion channels of the ion channel-containing structure between the measuring electrode and the reference electrodes can be determined and/or monitored.

An ion channel-containing structure in a solution may be guided towards a site on a substrate either by active or passive means. When the ion channel-containing structure makes contact with the site, e.g. substrate around an electrode, the contact surfaces form a high electrical resistance seal (a giga-seal) at the site, e.g. surrounding the electrode, so that an electrophysiological property of the ion channels can be measured using the respective electrode. Such electrophysiological property may be current conducted through the part of membrane of the ion channel-containing structure that is encircled by the giga-seal.

In the present context, the term "giga-seal" normally indicates a seal of a least 1G ohm, and this is the size of seal normally aimed at as a minimum, but for certain types of measurements where the currents are large, lower values may be sufficient as threshold values.

The whole-cell configuration may be obtained by applying, between the measuring electrode associated with each approved site and a reference electrode, a series of second electric potential difference pulses, monitoring a second current flowing between the measuring electrode and the reference electrode, and interrupting the series of second electric potential difference pulses whenever said second current exceeds a predetermined threshold value, thereby rupturing the part of the ion channel-containing structure which is closest to the measuring electrode.

Alternativelly, the whole-cell configuration may be obtained by subjecting the part of the ion channel-containing structure which is closest to the measuring electrode to interaction with a pore forming substance.

It should be noted that in the present context, the term "whole-cell configuration" denotes not only configurations in which a whole cell has been brought in contact with the substrate at a measuring site and has been punctured or, by means of a pore-forming substance, has been opened to electrical contact with the cell interior, but also configurations in which an excised cell membrane patch has been arranged so that the outer face of the membrane faces "upwardly", towards a test sample to be applied.

As the measuring electrode associated with a site is one of a plurality of electrodes on the substrate, and the ion channel-containing structure is one of many in a solution, it is possible to obtain many such prepared measuring set-ups on a substrate. A typical measurement comprises adding a specific test sample to the set-up, for which reason each measuring set-up is separated from other measuring set-ups to avoid mixing of test samples and electrical conduction in between set-ups.

BRIEF DESCRIPTION OF THE DRAWINGS

The present invention will now be described in greater detail with reference to the accompanying drawings, in which.

Figure 1:
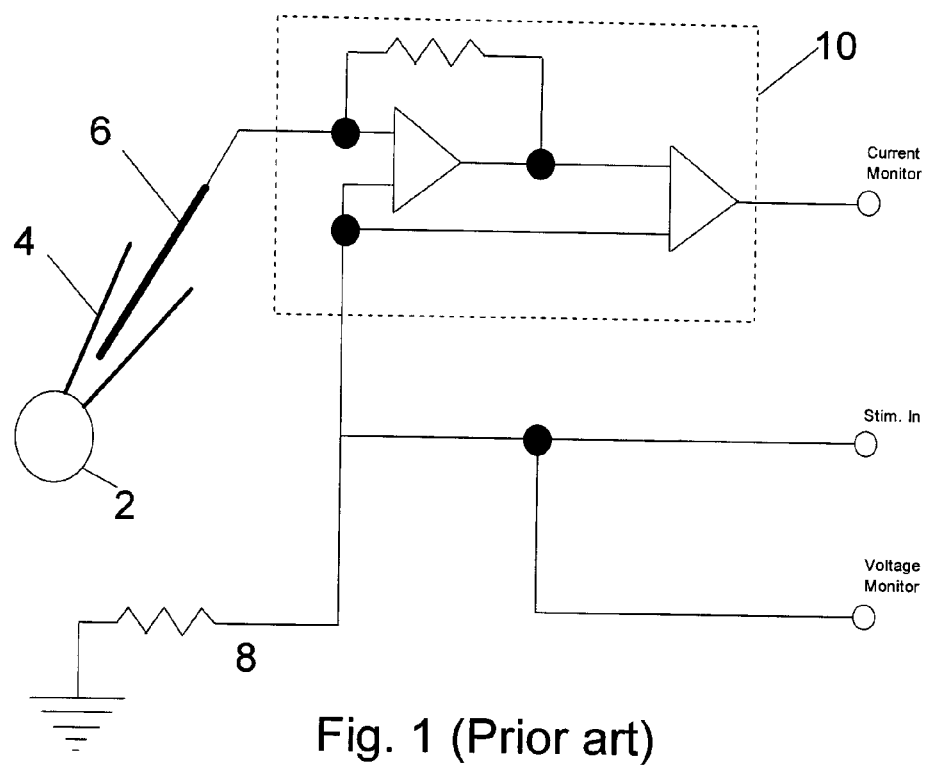
FIG. 1, as mentioned above, shows a diagram of a typical known electronic circuit for voltage clamp measurements.

The reference numbers in the drawings refer to the following:

| No. | Description |
| --- | --- |
| 2 | cell |
| 4 | pipette |
| 6 | pipette measuring electrode |
| 8 | reference electrode |
| 10 | voltage clamp amplifier |
| 11 | edge of hydrophobic region |
| 12 | substrate |
| 13 | substructure |
| 14 | site |
| 15 | test confinement |
| 16 | electrode |
| 17 | second structure part |
| 18 | lines of conducting material |
| 20 | contacts |
| 22 | insulating film |
| 24 | Silver |
| 26 | hydrophobic region |
| 28 | AgCl layer |
| 30 | aperture |
| 31 | $SiO_2$ layer |
| 32 | piping |

DESCRIPTION OF PREFERRED EMBODIMENTS

The present invention relates to a substrate with a plurality of electrodes at sites adapted to hold cells (or other ion channel-containing structures), such that the cell membrane and the substrate interface creates a giga-seal around an electrode, making it possible to determine or monitor electrophysiological properties of the cell membrane. It will be understood that when the term "cell" or "cell membrane" is used in the present specification, it will normally, depending on the context, be possible to use any other ion channel-containing structure, such as another ion channel-containing lipid membrane or an ion channel-containing artificial membrane. Electrophysiological properties can be, e.g., current flow through an ion channel or capacitance of an ion channel-containing membrane. It is possible to add individual test samples (typically pharmacological drugs) at each cell-holding location so that individual experiments can be carried out on each cell. An experiment can be to measure the response of the ion transfer channel to the addition of test sample. In order to carry out individual experiments, different test samples could be added to different cell-holding sites. One or more cell holding sites where a specific test sample is (going to be) added is hereafter called a test confinement.

The substrate of the invention will typically be a component used in an apparatus for carrying out measurements of the electrophysiological properties of ion transfer channels in lipid membranes such as cells.

The apparatus will be designed to provide means for carrying out a large number of individual experiments in a short period of time. This is accomplished by providing a microsystem having a plurality of test confinements each of which having sites comprising integrated measuring electrodes, and providing and suitable test sample supply. Each test confinement may comprise means for positioning cells, for establishment of giga-seal, for selection of sites at which giga-seal has been established, measuring electrodes and one or more reference electrodes. Thereby it is possible to perform independent experiments in each test confinement, and to control the preparation and measurements of all experiments from a central control unit such as a computer. Due to the small size of the test confinements, the invention permits carrying out measurements utilising only small amounts of supporting liquid and test sample. The present invention also provides several different procedures for carrying out measurements; these include measurements on fragments of cells and artificial membranes.

Figure 2A:
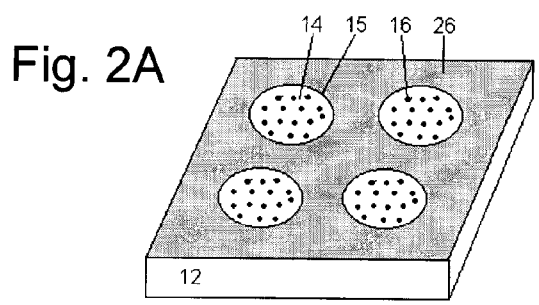
FIG. 2 shows a schematic view of examples of substrates having sites with electrodes for holding cell membranes or artificial membranes.
Figure 2B:
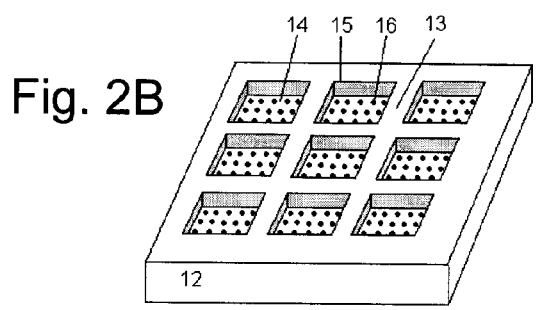
Figure 2C:
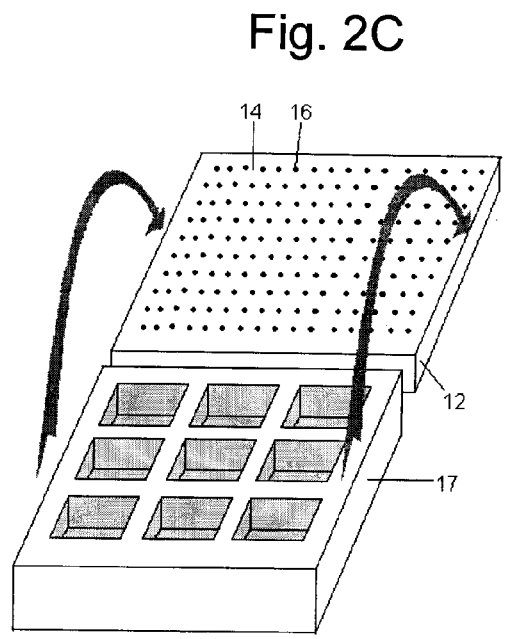

The substrate having sites with measuring electrodes (electrodes hereafter) can be designed in a number of ways, of which three are illustrated in FIGS. 2A–2C, and further ones are illustrated in FIGS. 3A–3D and 4A–4B. The distinction between the embodiments is the design of the sites on the substrate. Sites are adapted to hold an ion channel-containing structure, such as a cell, in that the surface material at the site is well suited for creating a seal with the cell (or structure) membrane as described in the prior art. Such materials include silicon, plastics, pure silica and other glasses such as quarts and pyrex or silica doped with one or more dopants selected from the group of Be, Mg, Ca, B, Al, Ga, Ge, N, P, As and oxides from any of these. The substrate proper can be made of any material suitable for a wafer processing technology, such as silicon, plastics, pure silica and other glasses such as quarts and pyrex or silica doped with one or more dopants selected from the group of Be, Mg, Ca, B, Al, Ga, Ge, N, P, As. Silicon is the presently preferred substrate material.

In the designs of FIGS. 2A–2C, the sites 14 are arranged on a locally flat surface of the substrate 12. Locally flat indicates that the surface of the substrate may have some substructure 13 on a scale larger than one or more sites, as seen in FIG. 2B. Sites, and thereby electrodes 16, can be arranged alone or in groups within this substructure.

The methods for production of the three designs of FIG. 2 are analogous to each other. FIG. 2A and 2B simply includes some subdivision of the basic design of FIG. 2C. The manufacture of the designs is now described with reference to FIGS. 3A and 6:

Lines 18 of conducting material are formed on the surface of the substrate by first depositing a layer of conducting material on the substrate. Deposition of materials on the substrate, and on other surfaces throughout the description, can be made using one of several deposition techniques, such as Physical Vapour Deposition which includes 1) application of material from a vapour phase, 2) spottering and 3) laser ablation; Chemical Vapour Deposition techniques which include 1) atmospheric pressure chemical vapour deposition (APCVD), 2) low pressure chemical vapour deposition (LPCVD), 3) plasma enhanced chemical vapour deposition (PECVD) and 4) photo enhanced chemical vapour deposition; as well as spin coating and growth techniques. Secondly, the individual wires are defined in a photolithography step, and thirdly, conducting material not being a part of the wires is removed by etching. The wires are preferably defined so that one part of the wires forms a line of contact pads 20 whereas another part forms an array of measuring electrode parts 16 and one or more reference electrodes 8. The array of electrode parts is not necessarily an ordered pattern. The contact pad and electrode part are preferably the two end parts of the wire, but may be any parts of e.g. a pattern of conducting strips. Preferably, the conducting material consists of metals or doped silicon.

Figure 7:
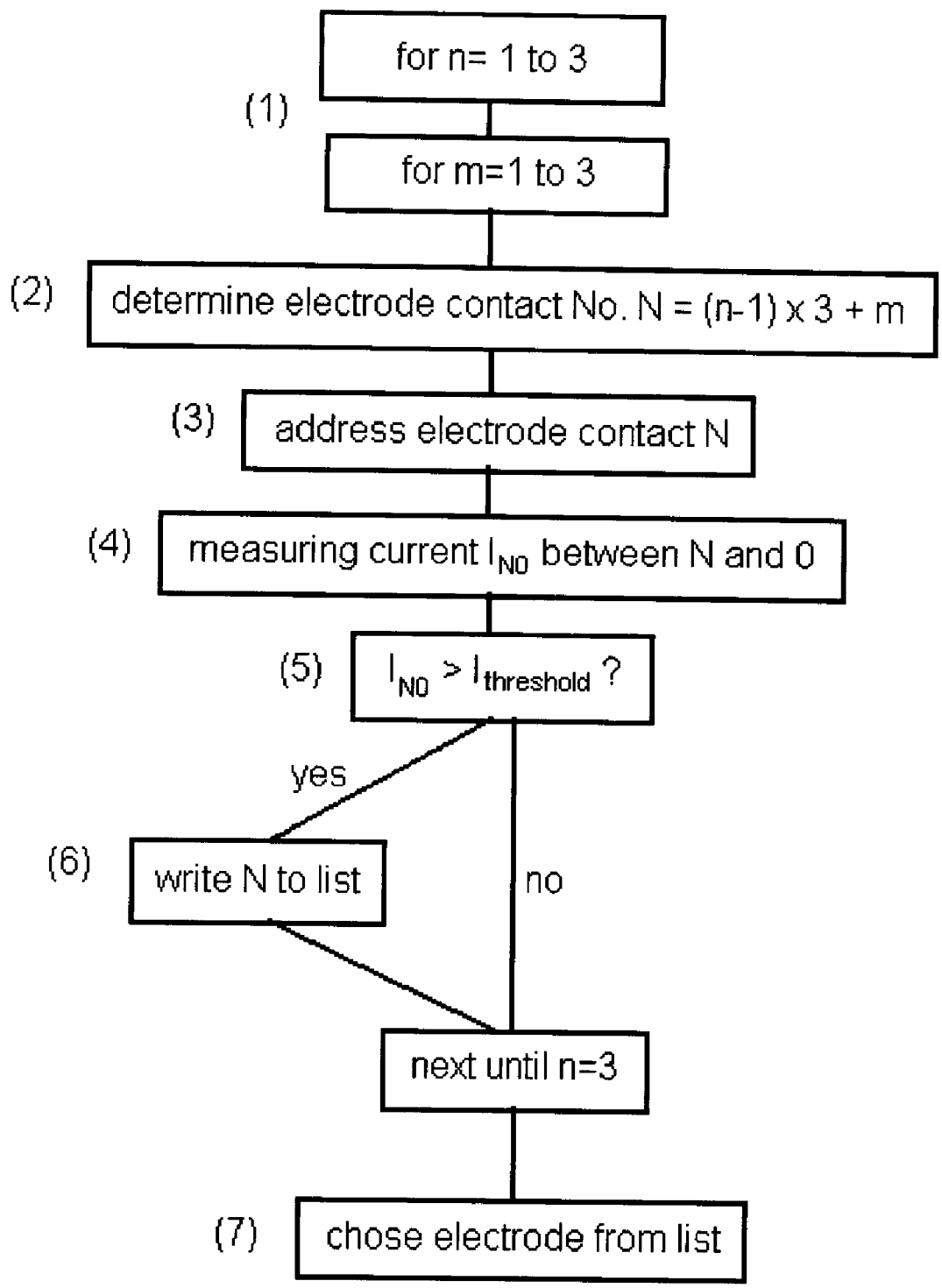
FIG. 7 shows a flow diagram of a procedure for detecting when a cell forms a giga-seal with an substrate, e.g. around an electrode.

In order to establish the electrodes and contacts, the conducting material not forming part of the electrode or of the contact part of each wire is covered with an insulating (hydrophilic) film 22, e.g. silicon dioxide, or multiple layers of silicon nitride and silicon dioxide. This is carried out by covering the whole surface with a layer of the insulating film using either thermal oxidation of silicon, physical or chemical vapour deposition, or spin coating. Using photolithography and an etching step, parts of the insulating film are removed to expose the wire and thereby form electrodes 16 and 8 and contacts 20. For a better electrical contact, electrodes (and contacts) can be covered with silver 24. Alternatively, lift-off techniques might be used in these cases where several layers of material are to be deposited in several thin layers. Here a photoresist is deposited over the substrate and the pattern to be formed is defined in the resist by illumination through a mask followed by etching. A layer of material, typically a metal, is vapour deposited onto the structure, and the photoresist is dissolved, thereby leaving metal in the defined pattern. At this stage, the substrate will appear as shown in FIG. 7, the thin lines 18 connecting electrodes and contacts being covered by insulating film.

Figure 3A:
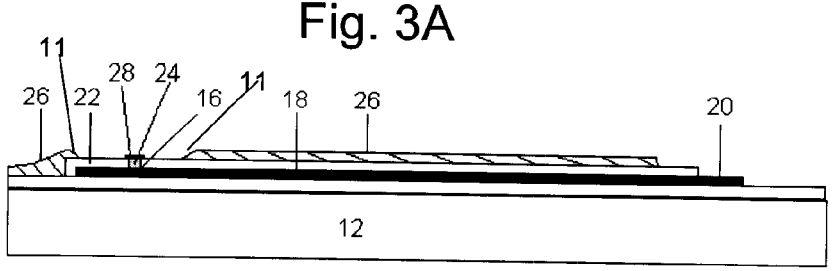
FIGS. 3A–3D shows cross-sectional side views of various embodiments of substrates of the invention, showing the different layers produced in wafer processing technology (deposition/photolithography/etching technology)

Optionally, but shown in FIG. 3A, hydrophobic regions 26 completely surrounding electrode sites or groups of sites are formed using a combination of deposition of a hydrophobic material like Teflon and photolithography. The hydrophobic material is deposited using either spin coating, chemical vapour deposition or plasma enhanced chemical vapour deposition. FIG. 2A shows a possible use of such regions. Finally, before use, a silver chloride layer 28 is formed on the electrode 16 using electrolytic treatment. The same procedure is normally followed for all measuring and reference electrodes in the substrates of the invention to establish them as silver/silver halide electrodes, such as silver/silver chloride electrodes.

Figure 3B:
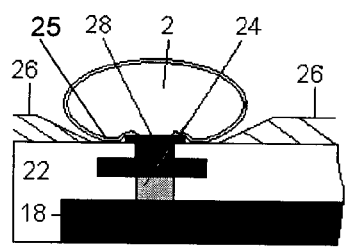
Figure 3C:
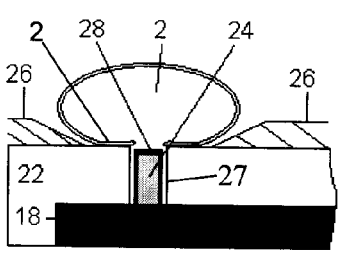
Figure 3D:
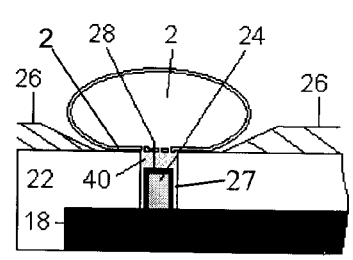

Using the same production scheme as described above, a number of different electrode designs shown in FIGS. 3B–3D can be applied. The designs shown imply some differences in the wafer processing described above, however, given the design, the adaptation of the wafer processing steps is obvious to the person skilled in wafer processing technology.

FIG. 3B shows a close-up of a site holding a cell 2 where the seal 25 is formed at the site surrounding the AgCl layer 28. In the production of the electrode, a large volume of AgCl layer 28 is formed on top of the silver 24 prior to deposition of the silica layer 22, thereby ensuring a large supply of AgCl.

FIG. 3C shows another embodiment wherein the measuring electrode is positioned in a small well 27 whereby the seal is formed between the membrane and the rim of the well 27. Depending on the size of the well 27, this embodiment allows for a greater separation of the membrane and the working electrode as well as for a larger volume of the carrier liquid surrounding the electrode.

FIG. 3D shows yet another embodiment wherein the working electrode is positioned in a small well 27 as in FIG. 3C. Here, a pore-forming substance 40 has been deposited at the site in order to establish, by the action of dissolved pore-forming substance on the cell, a whole-cell measuring configuration when a cell is positioned.

Figure 4A:
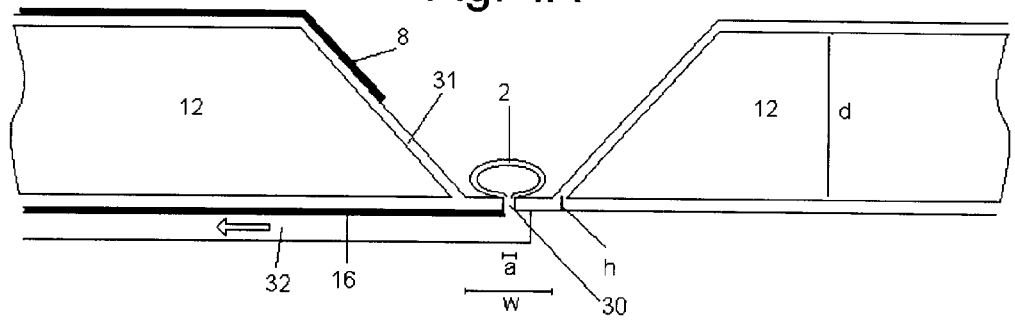
FIG. 4A shows a cross-sectional side view of another design for a substrate having sites with electrodes for holding cell membranes or artificial membranes.

In the design of FIG. 4A, a site is positioned at the bottom of a well, a geometrically shaped structure on the substrate. The function of the well is both to position the cell 2 at the site and to separate test confinements, which in this case consist of single sites.

A substrate with a well shaped as a truncated pyramid is shown in FIG. 4A, an aperture or passage 30 from the narrow end of the truncated pyramid to the bottom surface part of the substrate is also defined in the substrate, the well and the passage thereby creating a funnel. A measuring electrode 16 is provided on the bottom surface part of the substrate close to the aperture or passage, and a reference electrode 8 is provided at a side surfaces of the well, as shown in FIG. 4A. Preferably there is provided piping 32 for applying suction to the passage on the bottom side of the substrate. In a preferred embodiment, this piping leads to the upper'side of the substrate, and may include the electrical wiring to the measuring electrode.

When the term "bottom" is applied above, this merely refers to the orientation of the drawing. In the use of the substrate according to the invention, it is not a condition that the first surface part of the substrate is the upper surface part and the second surface part the lower surface part. In other words, gravity is not utilized to any substantial extent in connection with these very small structures, and, as an example, the design of FIG. 4A could also be used in an orientation corresponding to the figure having been rotated an angle of 180 degrees (or any other angle, for that matter).

The well shown in FIG. 4A is basically a truncated pyramidal cavity with a hole 30 at the apex. The base of the pyramid is a square. The top angle of the pyramid is 2×54.7°, the wafer thickness d=350–650 $\mu$m, the side-length at the apex of the pyramid is w≈30 $\mu$m in order to allow room for a cell. The apex of the pyramid is covered with a Silicon-dioxide membrane 31 of thickness h≈3 $\mu$m. In this membrane, a hole of diameter a≈0.1–10 $\mu$m, such as 1–5 $\mu$m, is formed.

The structure comprising a well or wells can be made in several quite different ways. Below, two different production processes for the basic structure are summarised, the .oxide first process and the oxide last process, respectively Oxide First Process Grow 3 $\mu$m wet thermal $SiO_2$ covering whole substrate.

Define the hole on the bottom side of the substrate by photomasking and Reactive Ion Etching to make the hole through the oxide to the silicon substrate.

Deposit LPCVD Silicon-nitride for an etch mask on both sides of the substrate.

Define nitride windows to form pyramid base plane on the upper side of the substrate by photomasking and Reactive Ion Etching and wet oxide etching (buffered Fluoric Acid)

Etch pyramidal cavities through the windows by anisotropic etching in the silicon. This creates pyramid sides with a slope of 54,7°.

Strip nitride etch stop using hot $H_3PO_4$.

Grow 1 $\mu$m wet thermal $SiO_2$ to electrically insulate the bulk silicon wafer in order to cover the sides of the pyramid. Other $SiO_2$ regions will not grow considerably.

Oxide Last Process

Form an etch-stop layer in silicon (boron doping) on the bottom side of the substrate, using either doping by implantation or epitaxial growth. The etch stop layer will typically be around 1 $\mu$m thick.

Deposit LPCVD silicon nitride for an etch mask on both sides of the substrate.

Define nitride windows to form pyramid base plane on the upper side of the substrate by photomasking and Reactive Ion Etching and wet oxide etching (buffered Fluoric Acid)

Etch pyramidal cavities through the windows by anisotropic etching in the silicon. This creates pyramid sides with a slope of 54,7°. The etching stops on the boron-doped etch stop to form an~1 $\mu$m thick silicon membrane.

Strip nitride etch stop using Hot $H_3PO_4$.

Define the hole on the bottom side by photomasking and Reactive Ion Etching of Silicon Grow wet thermal $SiO_2$ to convert the Silicon membrane into an oxide everywhere on the substrate. This process shrink the hole since $SiO_2$ is also formed inside the hole, which thereby can be made smaller compared to what is possible using photolithography.

For both production processes the main concern during processing is the mechanical stability of the $SiO_2$ membrane with the hole during the final high temperature oxidation step. The surface material (here $SiO_2$) can optionally be coated with silicon nitride, in order to prevent a contribution to the electrical conductivity.

Measuring and reference electrodes can now be formed. The measuring electrode on the bottom side can be formed using standard deposition and photolithography techniques. The reference electrode is preferably formed using evaporation of conducting material through a shadow mask, or through use of an electrophoretic resist technique.

Further, flow channel structures for adding liquid to the funnel may possibly be created in the substrate, giving an in-flow and an out-flow port to/from the funnel and elsewhere on the substrate. Alternatively, the flow channels are made on another substrate to be applied on top of the substrate, using normal etching techniques,.

Figure 4B:
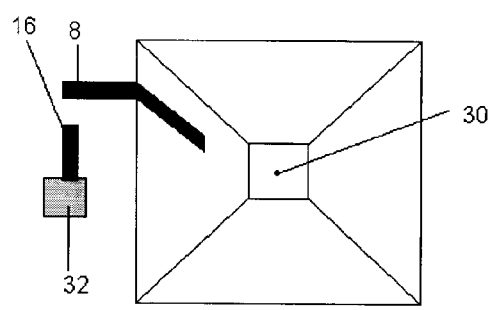
FIG. 4B shows a top view of the structure of FIG. 4A.

The features described are preferably arranged such that there is an easy access to all connection in- and outlets from above the assembly, as illustrated in FIG. 4B (suction outlet 32, contacts to measuring electrode 16 and reference electrode 8). This preferred configuration is adapted for applying a unit, having similar but reverse in- and outlets, on top of the assembly.

It is an important aspect that the substrate can provide some means for separating test confinements 15 as in FIG. 2. Test confinements preferably hold volumes as small as nanolitres. This is convenient considering the necessary amounts of the often expensive test samples; moreover, the time needed for mixing the solution by diffusion decreases with decreasing volume.

In FIG. 2A, the test confinements are defined using surface materials to define hydrophobic regions 26 and hydrophilic sites 14 on the substrate, as described previously. If the surface is wetted (but not flooded) by an aqueous solution such as saline, the liquid will confine itself to the hydrophilic areas, thereby defining the test confinements. Each hydrophilic area includes some sites 14 with electrodes 16 and may also include smaller scale hydrophobic areas.

On the substrate shown in FIG. 2B, the test confinements are separated by subdivisions 13 formed on the surface of the substrate. These subdivisions can be produced on the raw substrate by covering the substrate surface with a resist, and define the well openings using photolithography. An etch step followed by removal of the remaining resist leaves the substrate ready for formation of sites and electrodes.

FIG. 2C shows a substrate covered with electrodes, without any substantial subdivision. In this case the test confinements are defined using a structure part 17 with hollow subdivisions/chambers, to be applied on top of the substrate. By making a tight mechanical contact with the substrate, the structure part forms closed chambers each holding one or more sites with electrodes. If convenient, a similar structure part can be applied on top of any of the substrates shown in FIGS. 2A and B.

In all of the embodiments shown in FIG. 2, a reference electrode has to be located within each test confinement. This can be realised either by having an electrode at a site where no cell can cover it, an electrode so large that no cell can cover it, or, by dosing the number of cells in such a way that cells can not cover all electrodes. This last option allows for any of the measuring electrodes to function as reference electrode.

Depending on the specific shape of the substrate with electrodes, the addition of cell-supporting liquid and cells is carried out in one of the following ways. In a preferred embodiment, the test confinements are accessible from above, and droplets of supporting liquid and cells can be supplied at each test confinement by means of a dispensing or pipetting system. Systems such as an ink jet printer head or a bubble jet printer head can be used. Another possibility is an nQUAD aspirate dispenser or any other dispensing/pipetting device adapted to dose small amounts of liquid. Alternatively, supporting liquid and cells are applied on the substrate as a whole (e.g. by pouring supporting liquid containing cells over the substrate or immersing the substrate in such), thereby providing supporting liquid and cells to each test confinement. Since the volumes of supporting liquid and later test samples are as small as nanolitres, water vaporisation could represent a problem. Therefore, depending of the specific volumes, handling of liquids on the substrate should preferably be carried out in high humidity atmospheres.

In the case of the test confinements being closed chambers, they might only be accessible through a system of channels, i.e. a microliquid handling system. This is the case when a second structure part 17 (FIG. 2C) is applied on top of any of the substrates with or without test confinements. In this case supporting liquid and cells must be provided through inlet channels typically defined in the second structure part 17. Such a second structure part can be made of, e.g. silicon in which case flow channels can be formed using standard photolithography and etching techniques. Such a second structure part can be applied on top of any of the embodiments.

In another aspect, the cells are cultivated directly on the substrate, while immersed in growth medium. In the optimal case, the cells will form a homogeneous monolayer (depending on the type of cells to be grown) on the entire surface, except at regions where the surface intentionally is made unsuitable for cell growth. The success of cultivation of cells on the substrate depends strongly on the substrate material.

In still another aspect, an artificial membrane with incorporated ion channels may be used instead of a cell. Such artificial membrane can be made from a saturated solution of lipids, by positioning a small lump of lipid over an aperture. This technique is thoroughly described in e.g. "Ion Channel Reconstitution" by Christopher Miller, Plenum 1986, p. 577. If the aperture size is appropriate, and a polar liquid such as water is present on both sides of the aperture, a lipid bilayer can form over the aperture. The next step is to incorporate a protein ion channel into the bilayer. This can be achieved by supplying lipid vesicles with incorporated ion channels on one side of the bilayer. The vesicles can be drawn to fusion with the bilayer by e.g. osmotic gradients, whereby the ion channels are incorporated into the bilayer.

Obtaining good contact between the cell and a glass pipette, and thereby creating a giga-seal between a cell and the tip the pipette, is well described in the prior art. In order to draw the cell to the tip of the pipette, as well as to make the necessary contact for obtaining the giga-seal, it is normal to apply suction to the pipette.

In the case of the substrates described in FIGS. 2A–C, no suction is provided, and the positioning of the cells is carried out by other means. Moreover, it has been shown that the mere contact between the cell membrane and the substrate, typically ultra-pure silica, is sufficient for the cell to make some bonding to the surface and create a giga-seal.

Figure 5:
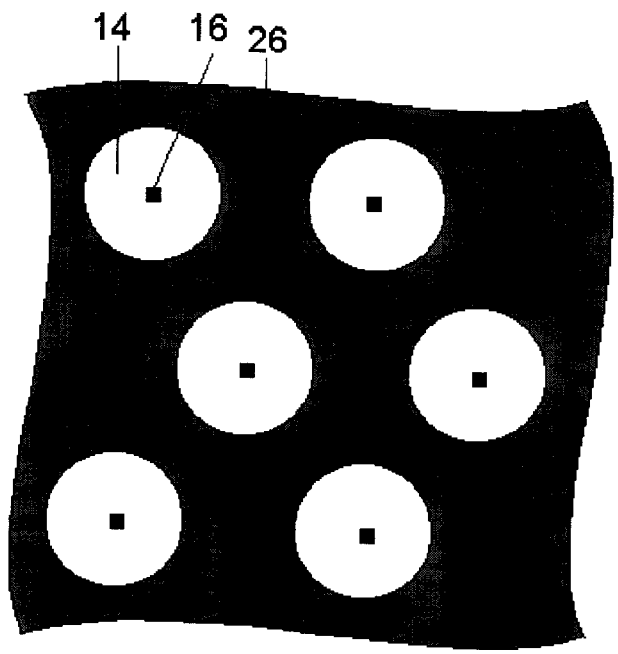
FIG. 5 shows a close-up of sites enclosed by a region of hydrophobic material.

The positioning can be carried out by electrophoresis, where an electric field from an electrode draws the charged cell towards it. Negatively charged cells will be drawn towards positive electrodes and vice versa. The electrostatic pull can also act as guiding means for a group of electrodes. Alternatively, within a test confinement, a hydrophobic material 26 may cover the surface of the substrate except at areas just around electrodes. This is shown in FIG. 5. Thereby, cells can only bind themselves on electrode sites 14. It is possible to apply both of these methods simultaneously or optionally in combination with a suitable geometrical shape of the substrate surface around electrodes, to guide the sinking cells towards the electrode.

In another embodiment, the density and pattern of sites and measuring electrodes is close to or higher than the density of cells when these are packed to make closest packing on the surface of the substrate. This ensures that when a sufficient number of cells is supplied, at least one electrode is covered by a cell without further guiding means.

In the embodiment shown in FIG. 4A, one or more cells 2 in a supporting liquid are applied and sink to the bottom end of the funnel, this being an example of positioning by geometrical shaping. If suction is applied, it draws the cell to the aperture 30 and establishes a connection between the cell and the aperture, creating a giga-seal separating the aperture inside and the solution. The giga-seal may take any form, e.g., circular, oval or rectangular. The supporting liquid makes electrical contact between the cell membrane and the reference electrode. The cell may be deformed by the suction, and a case where the cell extends into the aperture may be desired if controlled.

Each test confinement preferably holds several electrode sites. In order to detect whether an electrode is covered by a cell and insulated by a giga-seal, leak currents are measured between electrodes or between electrodes and the reference electrode. Even though a test confinement may include numerous electrodes, it is a simple task to search for electrodes insulated by giga-seals, a task well suited for a computer.

Figure 6:
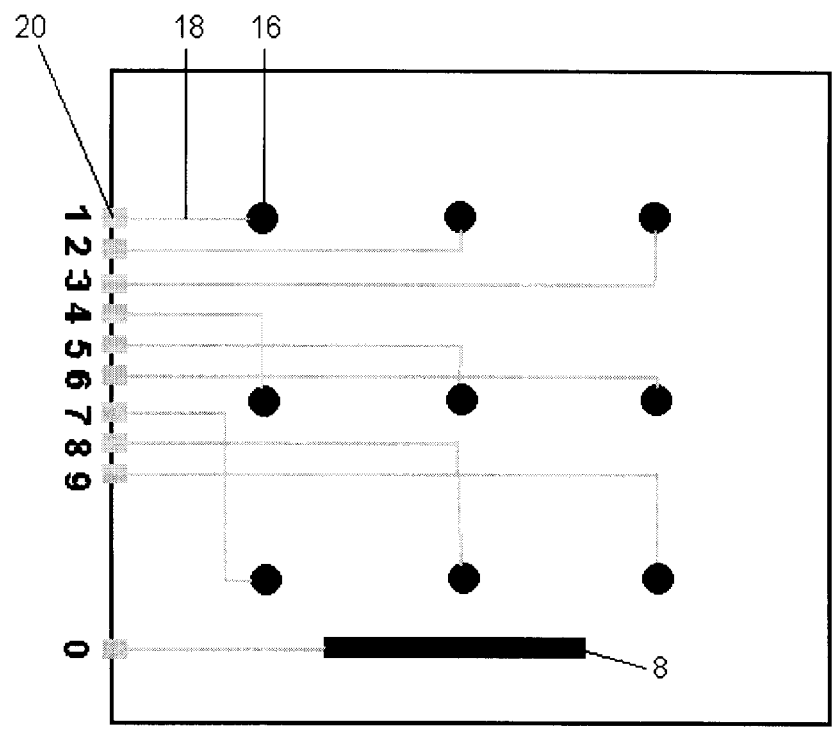
FIG. 6 shows a test confinement with an array of electrodes connected to a line of contacts.

FIGS. 6 and 7 proposes a scheme for doing so, where the electrodes 16 in a test confinement form an n×m matrix (here 3×3). The electrode connections 18 lead to a line of contacts 20 (No. 1 to 9) on the substrate that can be individually addressed by a computer with means for measuring currents. A list of giga-sealed electrodes can be made using a simple method sketched in the flow diagram of FIG. 7. First (1), two loops are established for going through all entries in the matrix of electrodes. In (2), the n×m array of the matrix is unfolded to provide an individual addressing (3) of electrode contacts with an electrode contact number N (No. 1 to 9). The current, at an applied voltage between contact N and the reference electrode 8, contact No. 0, is measured (4), and its value is compared to some threshold current $I_{threshold}$ (5) for determining whether the electrode is giga-sealed. If a giga-seal is detected, the contact number is added to a list of suitable electrodes (6) from which a measuring electrode is selected (7). This scheme carries some information on the relative positions n,m of suitable electrodes. This information can be used for selecting the optimal measuring electrode in (7), but can be omitted so that each electrode is simply known by its contact number N. Typically, only one electrode per test confinement is chosen.

The activity of these channels can be measured electrically (single channel recording) or, alternatively, the patch can be ruptured allowing measurements of the channel activity of the entire cell membrane (whole cell recording). High-conductance access to the cell interior for performing whole cell measurements can be obtained in at least 3 different ways (all methods are feasible, but various cells may work better with different approaches):

a) In the embodiment shown in FIG. 4A, the membrane can be ruptured by suction from the aperture side. Subatmospheric pressures are applied either as short pulses of increasing strength or as ramps or steps of increasing strength. Membrane rupture is detected by highly increased capacitative current spikes (reflecting the total cell membrane capacitance) in response to a given voltage test pulse.

b) Membrane rupture by applied voltage pulses. Voltage pulses are applied either as short pulses of increasing strength (mV to V) and duration (u- to msec), or as ramps or steps of increasing strength, between the electrodes. The lipids forming the membrane of a typical cell will be influenced by the large electrical field strength from the voltage pulses, whereby the membrane to disintegrates in the vicinity of the electrode. Membrane rupture is detected by highly increased capacitative current spikes in response to a given voltage test pulse.

c) Permeabilization of membrane. Application of pore-forming substances (for example antibiotics such as nystatin or amphotericin B), by e.g. prior deposition of these at the site. Rather than by rupturing the membrane, the membrane resistance is selectively lowered by incorporation of permeabilizing molecules, resulting in effective cell voltage control via the electrode pair. The incorporation is followed by a gradually decreasing total resistance and an increasing capacitance.

At this stage, a substrate with some electrodes each holding a cell is provided, the selected cells form a giga-seal around their respective electrodes, allowing for the electrode to measure electrophysiological properties of the ion transfer channels in the cell membrane. This represents the main aspect of the invention, the making available of a plurality of prepared sample cells for performing electrophysiological experiments. Moreover, each cell is confined in order to permit individual testing of the cells.

The remaining of this description will focus on the application of the substrate made ready in this way.

The test samples must be added to each test confinement individually, with different test samples for each test confinement. This can be carried out using the methods for applying supporting liquid, with the exception of the methods where supporting liquid are applied on the substrate as a whole.

Upon positioning the cell in a measuring configuration, several electrophysiological properties can be measured, such as current through ion channels (voltage clamp), or capacitance of ion channels containing membranes. In any case, a suitable electronic measuring circuit should be provided. The person skilled in the art will be able to select such suitable measuring circuit. One such possible circuit for voltage clamp measurements is described above with reference to FIG. 1.

In the case of voltage clamp measurements, the electrical current carried by the ion transfer channels in the cell membrane results in a charge transfer from the solution (reference electrode) to the measuring electrode, typically of the order of pA to $\mu A$ (picoampere–$10^{-12}$A). A low noise amplifier is provided for measuring these currents. The electronic circuits can be integrated in a separate standard unit having contact to the two electrodes and possibly flow channels for drug application.

What is claimed is:

1. An assembly, comprising:

a plane substrate having a first side and a second side spaced apart from one another and defining a first substrate thickness, and a first surface part and an opposite second surface part spaced apart from one another and defining a second substrate thickness, the second substrate thickness being less than the first substrate thickness, a plurality of sites in the first surface part of the substrate each of which is adapted to hold an ion channel-containing structure contained in a liquid, and each of which has a passage therein through the substrate connecting the first surface part and the second surface part, said passage having walls and being dimensioned to hold an ion channel-containing structure and to form a high resistance seal between said ion channel-containing structure and said substrate around or along the walls of said passage with the aid of suction, a plurality of measuring electrodes, each of which is associated with a respective site, one or more reference electrodes affixed to the substrate, wherein the measuring electrodes and the respective reference electrode or reference electrodes are electrodes capable of passing, when in electrolytic contact with each other and when a potential difference is applied between them, a current between them by delivery of ions by one electrode and receipt of ions by the other electrode, each of the sites being adapted to provide a high electrical resistance seal established between an area of contact of the outer surface of an ion channel-containing structure held at the site and a first surface part of the substrate around or along the walls of said passage, the seal, when established, separating a domain defined on one side of the seal established by the ion channel-containing structure and in electrolytic contact with the measuring electrode from a domain defined on the opposite side of the seal established by the ion channel-containing structure and in electrolytic contact with the respective reference electrode, whereby a current flowing between the reference and respective measuring electrodes and through the ion channel-containing structure can be determined and/or monitored, the electrodes being integrated with the assembly and having been formed by a photolithography, etching, and conducting thin film deposition process, connection means for connecting the substrate to a suction means for creating a suction on said ion channel-containing structure and through said passage so as to enable the ion channel-containing structure to be positioned, sealed and ruptured by the suction, wherein, in use, the first surface part is in contact with the liquid containing the ion channel containing structure, the connection means forming an integral part of the assembly and extending from the second surface part of the substrate to the first side of the substrate.

2. The assembly according to claim 1, wherein the substrate is a silicon substrate, and the surface part of the site with which the high electrical resistance seal is to be established is a silica surface part.

3. The assembly according to claim 1 or 2, wherein the plurality of sites is arranged in an array on the first surface part of the substrate.

4. The assembly according to claim 3, wherein the array of sites comprises at least 9 sites.

5. The assembly according to claim 1, wherein the measuring and reference electrodes are silver/silver halide electrodes.

6. The assembly according to claim 5, wherein the measuring and reference electrodes are silver/silver chloride electrodes.

7. The assembly according to claim 1, comprising a first layer of hydrophobic material positioned on or above the surface of the substrate, said first layer covering only parts of the surface of the substrate.

8. The assembly according to claim 7, where one or more sites are located within parts of the surface of the substrate not covered by said first layer.

9. The assembly according to claim 1, comprising one or more wells extending into the substrate and having well openings defined in the first surface part, each having a bottom part and a side part, at least some of the sites of the first surface part being positioned within the bottom parts of the wells.

10. The assembly according to claim 9, wherein the wells have been formed by a process comprising a photolithography/etching process.

11. The assembly according to claim 10, wherein the substrate is a silicon substrate, and wherein the wells are shaped as truncated pyramid the bottoms of which are constituted by the well openings and the side parts of which have a slope of 54.7°.

12. The assembly according to any of claims 9–11, wherein a reference electrode is positioned on the side part of each well.

13. The assembly according to claim 1, wherein the measuring electrode associated with each site is positioned at each respective site.

14. The assembly according to claim 13, wherein the measuring electrode at a site is positioned within the surface part of the site with which the high electrical resistance seal is to be provided.

15. The assembly according to claim 14, wherein the measuring electrode at a site is embedded in the substrate, and has a surface part which is substantially flush with the first surface part of the site with which the high electrical resistance seal is to be provided.

16. The assembly according to claim 14, wherein the measuring electrode at a site is embedded in the substrate, and has a surface part which is retracted from the first surface part of the site with which the high electrical resistance seal is to be provided.

17. The assembly according to claim 16, wherein the retracted surface part of the measuring electrode and the first surface part of the site with which the high electrical resistance seal is to be provided constitutes limitations of a volume, the volume being at least partly filled with a pore-forming substance.

18. The assembly according to claim 1, further defining, at each of the sites, a passage connecting the first and the second surface parts, the passage being positioned within the surface part of the site with which the high electrical resistance seal is to be provided.

19. The assembly according to claim 18, wherein the transverse dimension of the passage is 1–5 $\mu$m.

20. The assembly according to claim 18 or 19, wherein the measuring electrode associated with each site is positioned on the opposite second surface part of the substrate.

21. The assembly according to claim 20, wherein the measuring electrode associated with each site is positioned adjacent to an opening of the passage defined at the respective site.

22. The assembly according to claim 1, further comprising, for each of the sites, an electronic circuit that is connected with the respective measuring electrode and with the reference electrode or one of the reference electrodes for generation of an amplified signal that is a unique function of a current flowing through ion channels between said electrodes.

23. The assembly according to claim 1, wherein the plane substrate comprises a first substrate component and a second substrate component, wherein the first substrate component has a first face forming the first side of the plane substrate and an opposite face, the second substrate has a first face defining the second surface part of the plane substrate and an opposite face, and the first and second substrate components are connected to one another at their respective second faces.

24. A method of establishing a whole cell measuring configuration for determining and/or monitoring an electrophysiological property of one or more ion channels of one or more ion channel-containing structures, said method comprising the steps of:

providing an assembly comprising: a substrate having a first side and a second side spaced apart from one another and defining a first substrate thickness, and a first surface part opposite the second side and an opposite second surface part spaced apart from one another and defining a second substrate thickness, the second substrate thickness being less than the first substrate thickness, said substrate having a plurality of sites in the first surface part of the substrate, each of which is adapted to hold an ion channel-containing structure and each of which has a passage therein through the substrate connecting the first surface part and the second surface part, said passage having walls and being dimensioned to hold an ion channel-containing structure and to form a high resistance seal between said ion channel-containing structure and said substrate, around or along the walls of said passage, a plurality of measuring electrodes, each of said measuring electrodes being associated with a respective site, and one or more reference electrodes affixed to the substrate, the assembly further comprising connection means for connecting the substrate to a suction means, the connecting means extending from the second surface part to the first side of the substrate;

supplying a carrier liquid at one or more sites, said carrier liquid containing one or more ion channel-containing structures, the carrier liquid contacting the first surface part of the substrate, positioning at least one of the ion channel-containing structures at a corresponding number of sites;

forming a high electrical resistance seal between an area of contact of the outer surface of an ion channel-containing structure held at the site and a first surface part of the substrate around or along the walls of said passage by applying a suction to said passage via said connection means, the seal, when established, separating a domain defined on one side of the seal established by the ion channel-containing structure and in electrolytic contact with the measuring electrode from a domain defined on the opposite side of the seal established by the ion channel-containing structure and in electrolytic contact with the respective reference electrode;

checking for a high electrical resistance seal between an ion channel-containing structure held at a site and the first surface part of the substrate around or along the walls of said passage with which the high electrical resistance seal is to be established by successively applying a first electric potential difference between the measuring electrode associated with the site and a reference electrode, monitoring a first current flowing between said measuring electrode and said reference electrode, and comparing said first current to a predetermined threshold current and, if the first current is at most the predetermined threshold current, then approving the site as having an acceptable seal between the ion channel-containing structure and the first surface part of the site; and establishing a whole-cell configuration at approved sites, whereby a third current flowing through ion channels of the ion channel-containing structure between the measuring electrode and the reference electrodes can be determined and/or monitored.

25. The method according to claim 24, wherein the step of establishing a whole-cell configuration at approved sites comprises applying, between the measuring electrode associated with each approved site and a reference electrode, a series of second electric potential difference pulses, monitoring a second current flowing between the measuring electrode and the reference electrode, and interrupting the series of second electric potential difference pulses whenever said second current exceeds a predetermined threshold value, thereby rupturing the part of the ion channel-containing structure which is closest to the measuring electrode.

26. The method according to claim 24, wherein the step of establishing a whole-cell configuration at approved sites comprises subjecting the part of the ion channel-containing structure which is closest to the measuring electrode to interaction with a pore forming substance.

27. The method according to any of claims 24–26, wherein the measuring electrode associated with each site is positioned at each respective site, and wherein the step of positioning at least one of the ion channel-containing structures at one or more sites comprises applying a third electric potential difference between one or more measuring electrodes and one or more reference electrodes for generating an electric field moving ion channel-containing structure or structures towards the at least one measuring electrode for positioning ion channel-containing structures at the site.

28. The method according to any of claims 24–26, wherein the substrate defines, at each of the sites, a passage connecting the first and the second surface parts, the passage being positioned substantially in a middle part of the surface part of the site with which the high electrical resistance seal is to be provided, and wherein the step of positioning one or more ion channel-containing structures at one or more sites comprises the step of subjecting an internal volume of the passage of a selected site to a suction generating a flow of carrier liquid through the passage for guiding ion channel-containing structures towards the passage.

* * * * *